US006916286B2

(12) United States Patent
Kazakevich

(10) Patent No.: US 6,916,286 B2
(45) Date of Patent: Jul. 12, 2005

(54) ENDOSCOPE WITH IMAGING PROBE

(75) Inventor: Yuri Kazakevich, Andover, MA (US)

(73) Assignee: Smith & Nephew, Inc., Memphis, TN (US)

(*) Notice: Subject to any disclaimer, the term of this patent is extended or adjusted under 35 U.S.C. 154(b) by 259 days.

(21) Appl. No.: 09/925,826

(22) Filed: Aug. 9, 2001

(65) Prior Publication Data
US 2003/0032863 A1 Feb. 13, 2003

(51) Int. Cl.[7] .............................................. A61B 1/05
(52) U.S. Cl. ...................... 600/173; 600/157; 600/129
(58) Field of Search ................................. 600/157, 109, 600/137, 192, 146, 173, 112, 129; 348/65, 82–85

(56) References Cited

U.S. PATENT DOCUMENTS

| | | | |
|---|---|---|---|
| 4,855,838 A | 8/1989 | Jones et al. | |
| 4,858,001 A | 8/1989 | Milbank et al. | |
| 5,028,997 A | 7/1991 | Elberbaum | |
| 5,111,288 A | 5/1992 | Blackshear | |
| 5,166,787 A | 11/1992 | Irion | |
| 5,305,121 A | 4/1994 | Moll | |
| 5,381,784 A | 1/1995 | Adair | |
| 5,508,735 A | 4/1996 | Mueller | |
| 5,575,757 A | 11/1996 | Kennedy et al. | |
| 5,604,531 A | 2/1997 | Iddan et al. | |
| 5,653,677 A | 8/1997 | Okada et al. | |
| 5,797,836 A | 8/1998 | Lucey et al. | |
| 5,827,323 A * | 10/1998 | Klieman et al. | ............. 606/205 |
| 5,894,369 A | 4/1999 | Akiba et al. | |
| 5,989,182 A | 11/1999 | Hori et al. | |
| 6,007,484 A | 12/1999 | Thompson | |
| 6,097,423 A * | 8/2000 | Mattsson-Boze et al. | ..... 348/65 |
| 6,371,909 B1 * | 4/2002 | Hoeg et al. | .................. 600/173 |
| 6,402,686 B1 | 6/2002 | Ouchi | |

FOREIGN PATENT DOCUMENTS

| | | | |
|---|---|---|---|
| EP | 0497347 A3 | 8/1992 | |
| EP | 0497347 A2 | 8/1992 | |
| GB | 2339926 | 2/2000 | |
| WO | WO 93/15648 * | 8/1993 | ............ A61B/1/06 |
| WO | 96/05693 | 2/1996 | |
| WO | WO 97/11634 | 4/1997 | |
| WO | WO 98/32380 | 7/1998 | |
| WO | WO 00/57770 | 10/2000 | |
| WO | WO 00/57770 A3 | 10/2000 | |
| WO | 01/49164 | 7/2001 | |

OTHER PUBLICATIONS

PCT International Search Report for International Application No. PCT/US 02/24809.
PCT Invitation to Pay Additional Fees including Communication Relating to the Results of the Partial International Search Report of International Application No. PCT/US 02/24809.

* cited by examiner

Primary Examiner—John P. Leubecker
(74) Attorney, Agent, or Firm—Fish & Richardson P.C.

(57) ABSTRACT

An endoscope includes an imaging probe, positioned at the distal end of the elongated member; a pivot mechanism mechanically coupled to the imaging probe; and an actuating assembly extending through the passage of the elongated member and coupled to the pivoting mechanism. The imaging probe includes an objective lens, an imager positioned to receive an image from the objective lens, and a light source for illuminating a target. Upon actuation of the actuating mechanism, the pivot mechanism rotates the imaging probe relative to a point at the distal end of the elongated member.

22 Claims, 10 Drawing Sheets

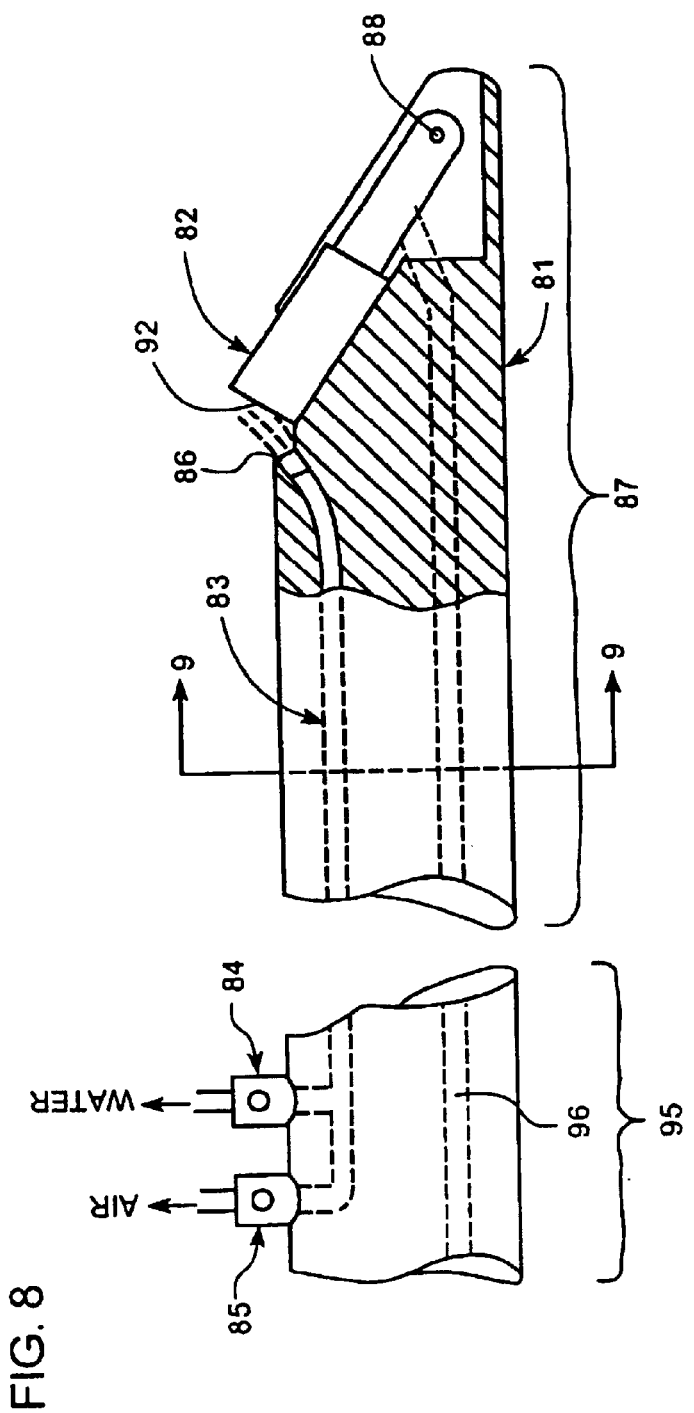
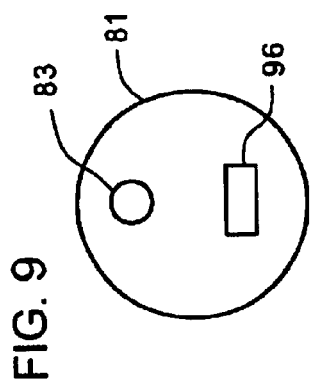
FIG. 8
FIG. 9

ENDOSCOPE WITH IMAGING PROBE

TECHNICAL FIELD

This invention relates to endoscopes, and more particularly to endoscopes having imaging probes.

BACKGROUND

The invention relates to endoscopes, and in particular, endoscopes that have imaging probes. Endoscopes are widely used to inspect regions of the body (e.g., cavities, joints) during surgery (such as laparoscopic/thoracoscopic surgery) through a small puncture. Typically, the endoscope includes an elongated insertion tube equipped with a set of optical fibers that extend from a proximal handle through the insertion tube to the distal viewing tip of the endoscope. An external light source provides light to the optical fibers via a cable that rigidly attaches to the handle (e.g., at a post on the side of the handle) of the endoscope.

An optical image of the target is collected by one or more lenses mounted in the distal viewing tip of the endoscope and is passed to, e.g., a solid-state image detector (such as a charge-coupled-device (CCD)). The CCD converts the received optical image to electrical signals that are processed for viewing on a display.

Some endoscopes have a direction of view (i.e., the direction along which the endoscope emits and receives light) along the longitudinal axis of the insertion tube. The distal viewing ends of other endoscopes are constructed to provide an off-axis direction of view (e.g., at 30 degrees or at 70 degrees).

SUMMARY

The invention features an endoscope having an elongated member with a longitudinal axis and a passage extending from a proximal end to a distal end of the endoscope.

In a first aspect of the invention, the endoscope includes an imaging probe, positioned at the distal end of the elongated member; a pivot mechanism mechanically coupled to the imaging probe; and an actuating assembly extending through the passage of the elongated member and coupled to the pivoting mechanism. The imaging probe includes an objective lens, an imager positioned to receive an image from the objective lens, and a light source for illuminating a target. Upon actuation of the actuating mechanism, the pivot mechanism rotates the imaging probe relative to a point at the distal end of the elongated member.

Embodiments of the invention may have one or more of following features. The endoscope can be rotated about its longitudinal axis. The pivoting mechanism includes an arm that swivels about the point. An alternative power source and a transceiver can be positioned in the distal end of an endoscope where the transceiver can receive signals from the transmitter in the imaging probe and relay those signals to a receiver. The actuating mechanism may include a chain and a sprocket located at the distal end of the elongated member and the sprocket is coupled to a chain. Alternatively, the actuating mechanism can be a push rod. The actuating assembly could also be in the form of a rack and pinion assembly. The rotation of the imaging probe, attached to a pivot mechanism at the distal end, allows the surgeon to view the target object and to "look back" towards the incision point.

The actuating mechanism includes a rotatable ring positioned at the proximal end of the elongated member. The elongated member includes a conduit with a first port at a proximal end of the elongated member and attached to a fluid source and a second port at a distal end of the elongated member and positioned to discharge fluid on the objective lens. An endoscope having a conduit connected to a fluid source is advantageous in embodiments in which the imaging probe is rotatable to a retracted profile. In this embodiment, the objective lens can be cleaned without removing the endoscope from the surgical operation by spraying fluids directly on the objective lens. The conduit has a third port at the proximal end of the elongated member and connected to an air source used, for example, to dry the objective lens.

The imaging probe includes a transmitter and a first power source electrically connected to the transmitter. The endoscope has a transceiver located at the proximal end of the elongated member that receives signals from the transmitter and transmits the signals to a receiver that is external to the endoscope. The endoscope has a second power source positioned at the proximal end of the elongated member and electrically connected to the transceiver. By having less wires than conventional endoscopes, the endoscope can be made smaller or, due to the space made available, include more design features.

In another aspect of the invention, an endoscope includes an imaging probe, positioned at the distal end of the elongated member, and having an objective lens, an imager positioned to receive an image from the objective lens, a transmitter electrically connected to the imager, a light source for illuminating a target first power source, and a first power source for supplying power to the transmitter and the light source.

Embodiments of this aspect of the invention may include one or more of the following features. The endoscope includes a pivot mechanism mechanically coupled to the imaging probe; and an actuating assembly extending through the passage of the elongated member and coupled to the pivoting mechanism. Upon actuation of the actuating mechanism, the pivot mechanism rotates the imaging probe relative to a point at the distal end of the elongated member. Other embodiments of this aspect include one or more of the embodiments described in the first aspect of the invention.

Because the transmitter and light source are positioned within the imaging probe, the number of electrical and optical cables needed for providing electrical power and light, respectively, can be minimized and possibly eliminated. An endoscope with a reduced number of cables is much easier to manipulate. Other advantages include those discussed above in conjunction with the first aspect of the invention.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 8 is a cross-sectional side view of still another alternative embodiment of an endoscope with an air and water duct for cleaning an objective lens of the imaging probe.

FIG. 9 is a cross-sectional end view of the endoscope along lines 9—9 of FIG. 8.

DETAILED DESCRIPTION

Figure 1A:
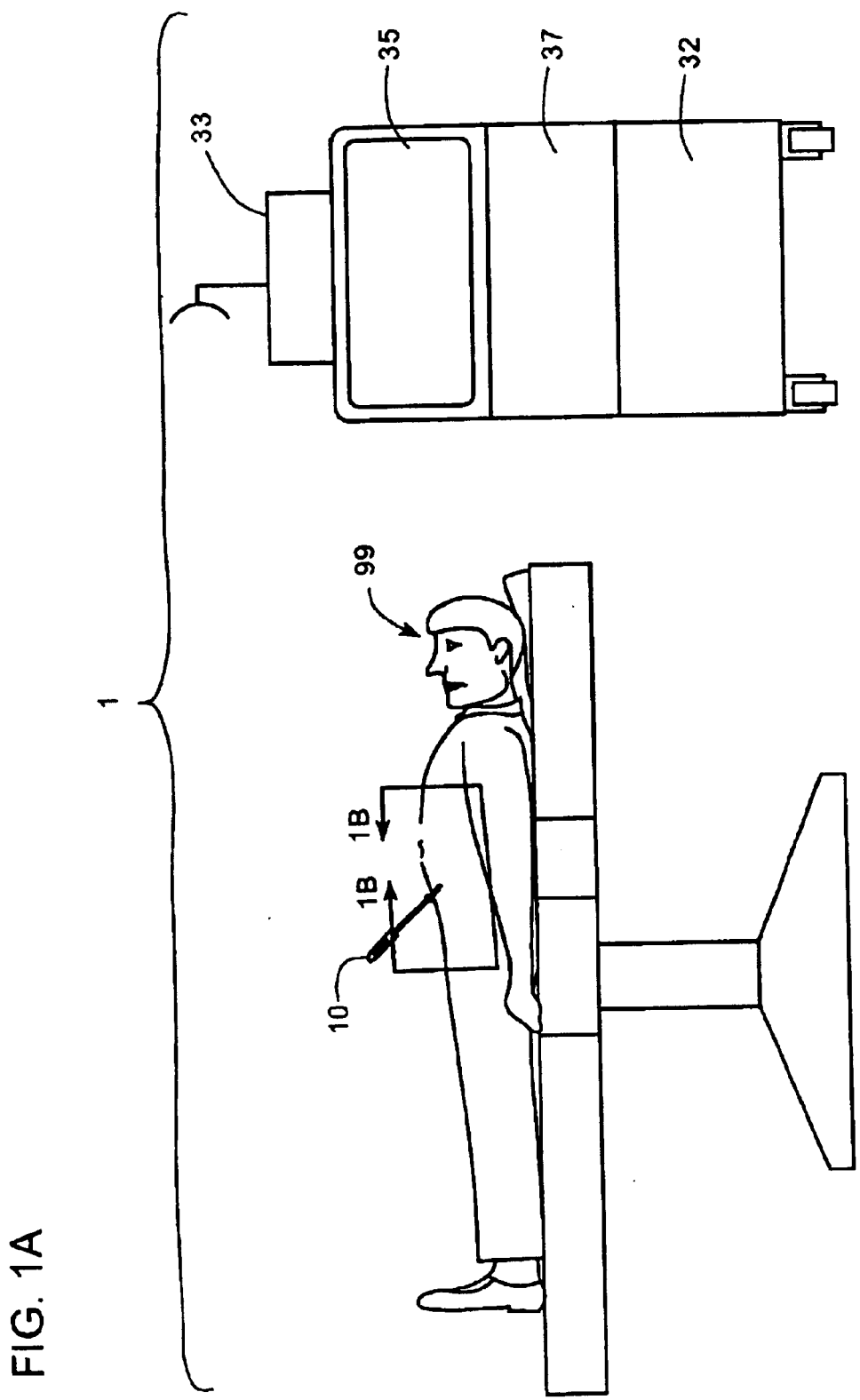
FIG. 1A shows an endoscopic system including an endoscope in accordance with the invention.
Figure 1B:
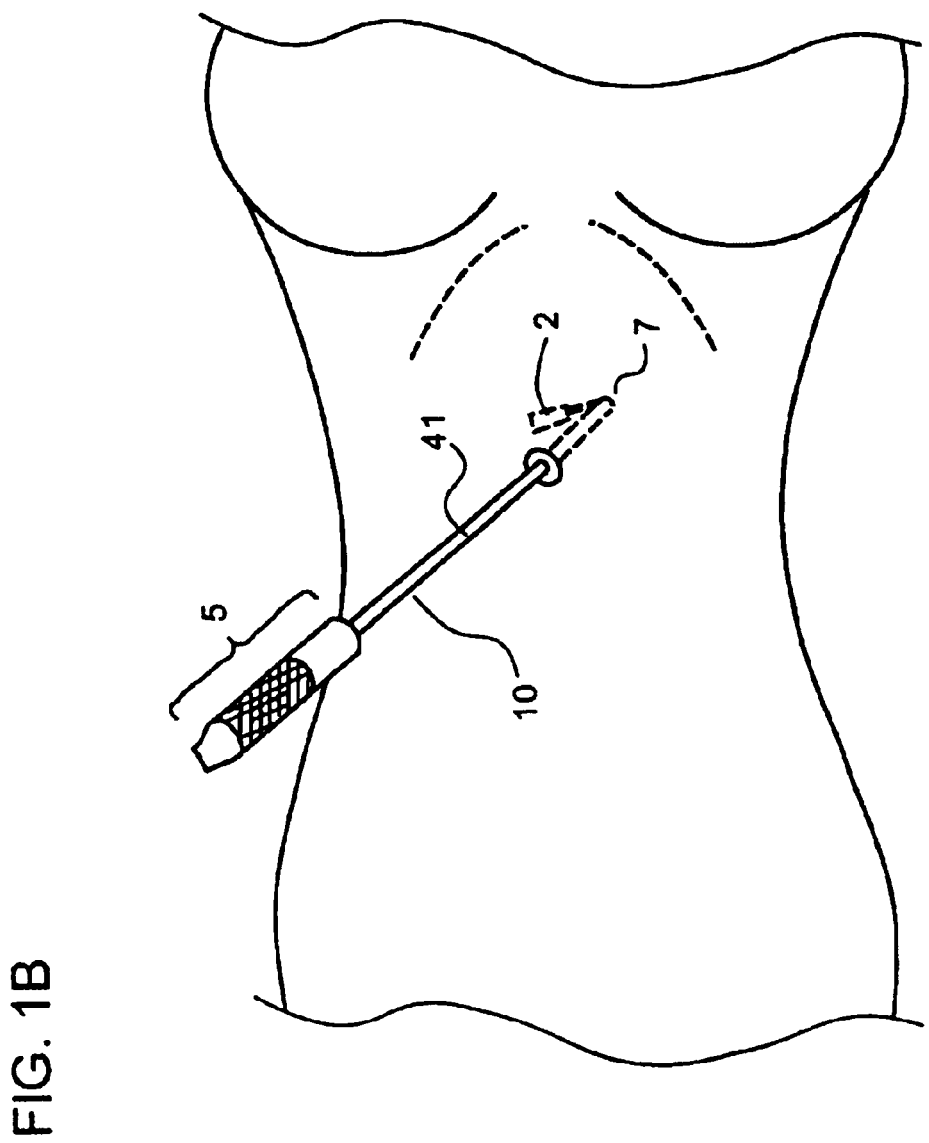
FIG. 1B is an enlarged view of the area of the endoscopic system enclosed by line 1B—1B of FIG. 1A.

Referring to FIGS. 1A and 1B, an endoscopic system 1 is shown in use in a surgical procedure performed on a patient 99. Endoscopic system includes a wireless endoscope 10, which transmits radio frequency signals, representative of images of an object under view (e.g., tissue within the patient's abdomen), to a control unit 32. Control unit 32 includes an external receiver 33 for receiving the radio frequency signals from endoscope 10 and circuitry (not shown) for converting the radio frequency signals into video signals for viewing on a display monitor 35. Control unit 32 also includes a data storage unit 37 for storing programming software as well as digital representations of the images. As shown in FIG. 1B, endoscope 10 includes an imaging probe 2 positioned at a distal end 7 of a hollow elongated shaft 41. Elongated shaft 41 extends through an incision point in the abdomen of patient 99 and is attached to a handle 5 at the proximal end of endoscope 10.

Figure 2:
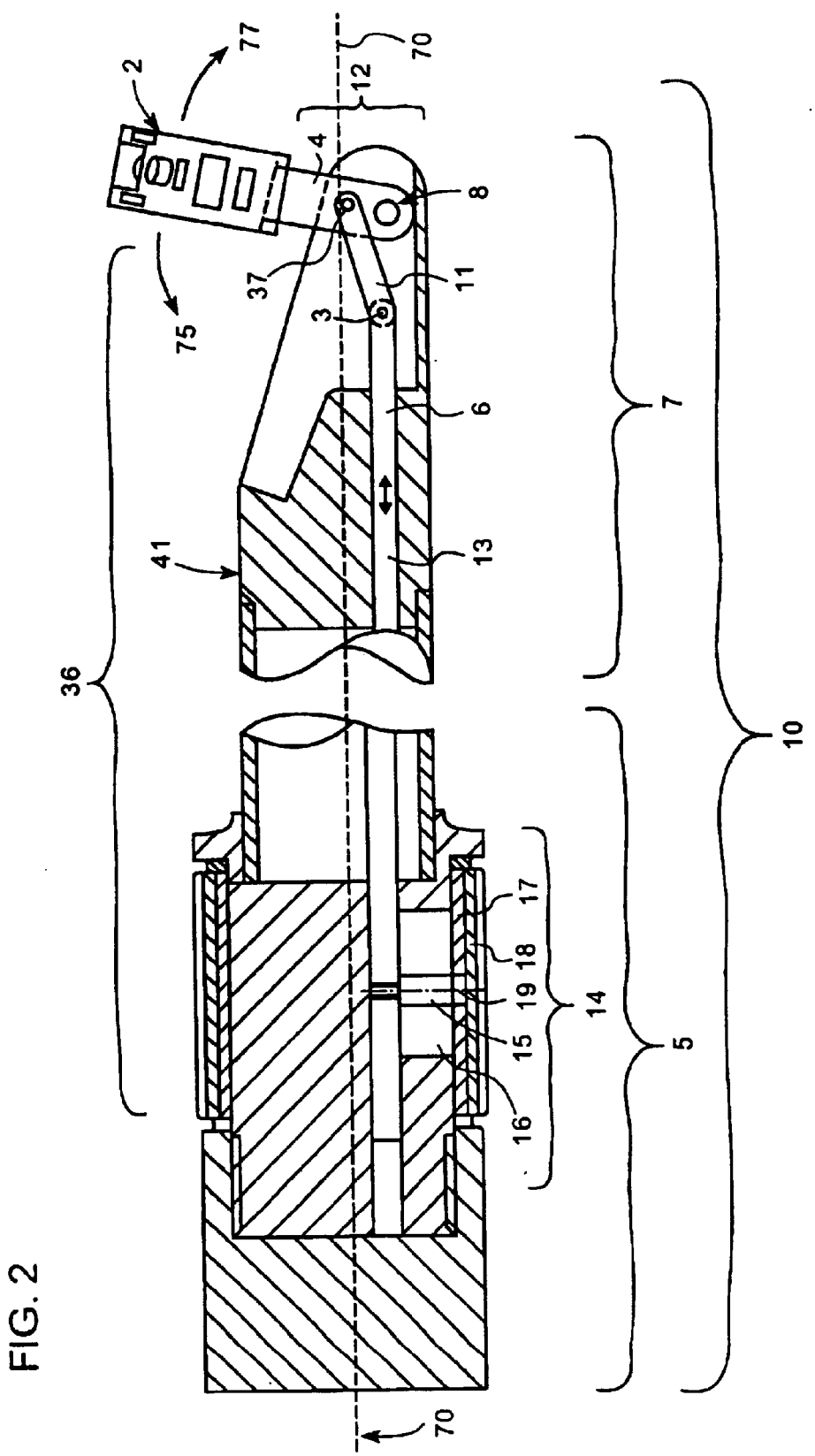
FIG. 2 is a cross-sectional side view of the endoscope of FIG. 1B in a partially extended position.

Referring to FIG. 2, imaging probe 2 is rotatable through the use of a pivot mechanism 12 at the distal end 7 of hollow elongated shaft 41. Handle 5 permits the user to position distal end 7 of elongated shaft 41 appropriately within the body and also houses a rotator mechanism 14 (described in greater detail below) which functions as an actuating mechanism. Because imaging probe 2 is rotatable about distal end 7, the surgeon can advantageously focus on the target object and surrounding areas. In certain embodiments, the surgeon is able to obtain a view back towards the incision point. The ability to rotate the imaging probe in this manner is particularly advantageous in laparoscopic/thoracoscopic surgical procedures.

Endoscope 10 includes an actuating assembly 36 having both a push rod 6 extending between and mechanically coupling the rotator mechanism 14 and pivoting mechanism 12. Rotator mechanism 14 includes an inner ring 17 having a helical groove 19 that extends substantially along the length of the inner ring and along a longitudinal axis 70 of the endoscope. Helical groove 19 is aligned with a horizontal slot 16 formed within elongated shaft 41. Inner ring 17 is surrounded by an outer adjustment ring 18 which forms the rotatable part of handle 5 used by the surgeon to move imaging probe 2 at the distal end of endoscope 10. Outer adjustment ring 18 is mechanically coupled to push rod 6 using a pin 15 that extends through helical groove 19 and horizontal slot 16. Horizontal slot 16 restricts the movement of pin 15 along the axis 70 and prevents it from rotating. Helical groove 19 travels approximately 135° around ring 17 and has a width slightly larger than the diameter of pin 15. Counterclockwise (arrow 75) and clockwise (arrow 77) rotation of adjustment ring 18 causes push rod 6 to move axially away and toward the distal end of endoscope 10, respectively. The axial motion of push rod 4 causes imaging probe 2 to swivel about a fixed point 8 at the distal end of endoscope 10. A rotator mechanism of this type is described in U.S. Pat. No. 5,575,757, which is incorporated herein by reference.

Push rod 6 includes a proximal section 13 extending along axis 70 and having an end attached to pin 15 of the rotator mechanism 14. Push rod 6 also includes a distal section pivotably connected (e.g., with a pin) to an opposite end of proximal section 13 at a joint 3. Distal section 11 is also pivotably connected (e.g., with a pin) to an arm 4 of pivot mechanism 12 at a connection point 37. When outer adjustment ring 18 is rotated, pivot mechanism 12 causes arm 4 to rotate about fixed point 8. Fixed point 8 may be a fastener (e.g., screw or rivet) that is fixed to the distal end 7 of elongated shaft 41 and pivotably attached to arm 4. Because connection point 37 is spaced away from fixed point 8, movement of push rod 6 is easier. Imaging probe 2 is detachably secured to arm 4 so that imaging probe 2 can be easily removed from arm 4 for replacement or for repair.

Figure 3A:
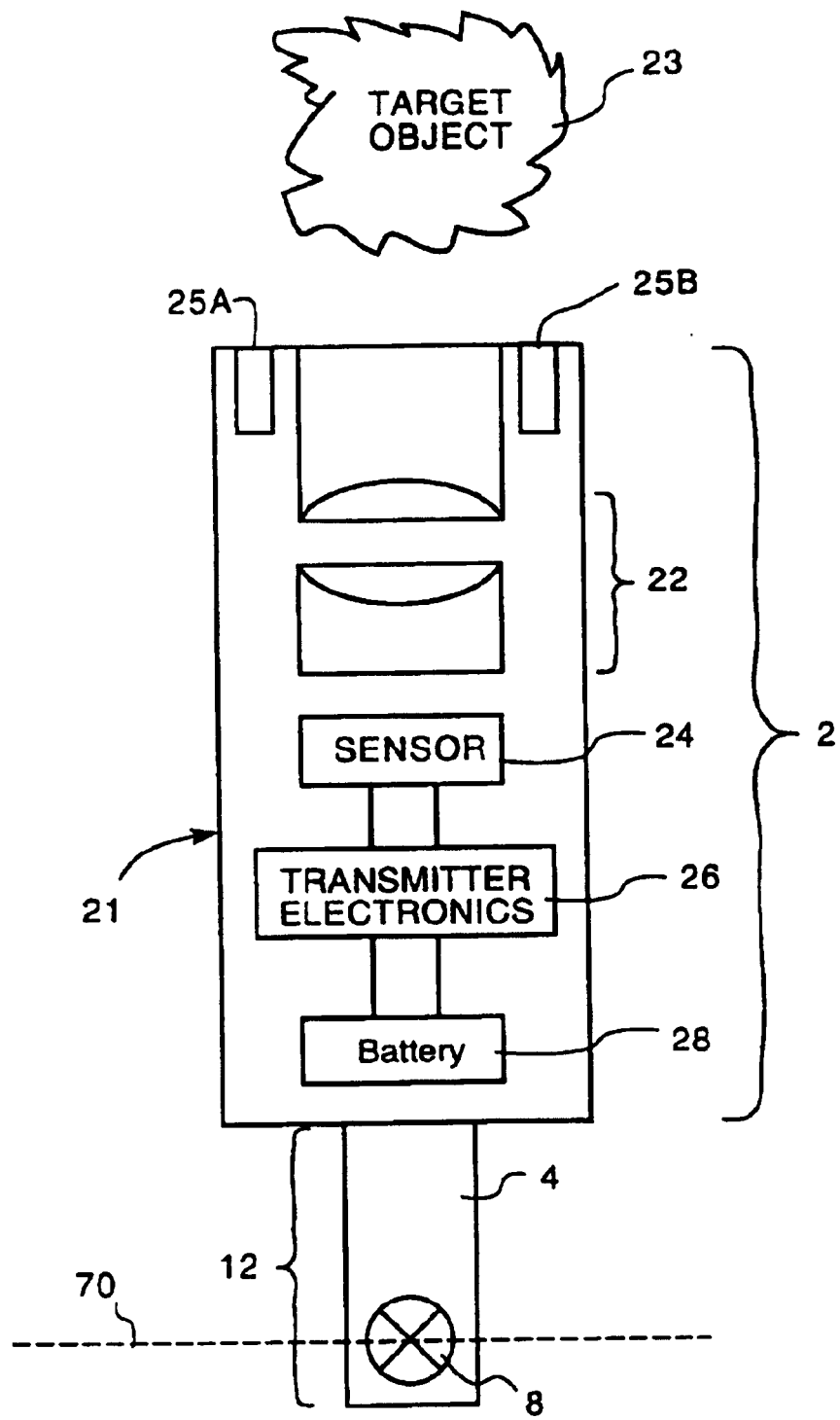
FIG. 3A is a schematic representation of an imaging probe portion of the distal end of the endoscope of FIG. 2.
Figure 3B:
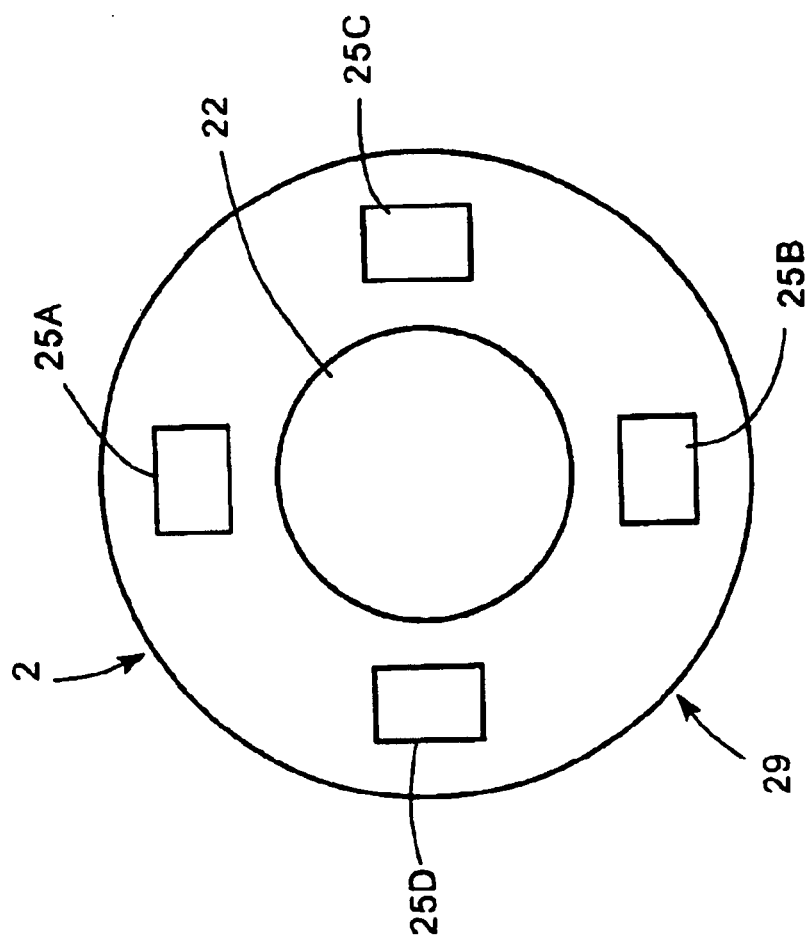
FIG. 3B is an end view of the of the imaging probe.

Referring to FIGS. 3A–3B, imaging probe 2 has an objective lens system 22, a sensor 24 (e.g., a charge-coupled device, CMOS imager), a battery 28, a transmitter 26, and an illumination source 25 that are all enclosed within a housing 21. Illumination source 25 includes here four light emitting diodes (LEDs) (e.g., LED 25a, LED 25b, LED 25c and LED 25d) equally spaced apart by 90° along a perimeter 29 of the exposed end of imaging probe 2. Battery 28 supplies power to transmitter 26, illumination source 25, and sensor 24.

Objective lens 22 system can be either a single lens or a combination of several lenses that light passes through to form an image on sensor 24. The distal end of objective lens system 22 is recessed within housing 21 to protect the exposed exterior surface of the objective lens system and has a field of view typical of endoscope devices (e.g., 75° to 110°).

During operation, illumination sources illuminate outwardly all areas within its unobstructed illumination range including a target object 23. Images of target object 23 are reflected back through objective lens system 22 and on sensor 24 where the images are converted into electrical signals. Transmitter 26 receives the electrical signals and converts them into, for example, radio frequency (RF). Receiver 33 receives the RF signals and processes them for viewing on monitor 35. Because objective lens system 22, sensor 24, battery 28, transmitter 26, and illumination source 25 are all enclosed within housing 21, imaging probe 2 constitutes a fully autonomous imaging unit. With this configuration, the number of electrical and optical cables needed for providing electrical power and light can be reduced, thereby allowing the surgeon to more easily manipulate endoscope 10. Other embodiments can have more or less LEDs spaced around perimeter 29 of imaging probe 2 as illumination requirements and power limitations allow.

Figure 4:
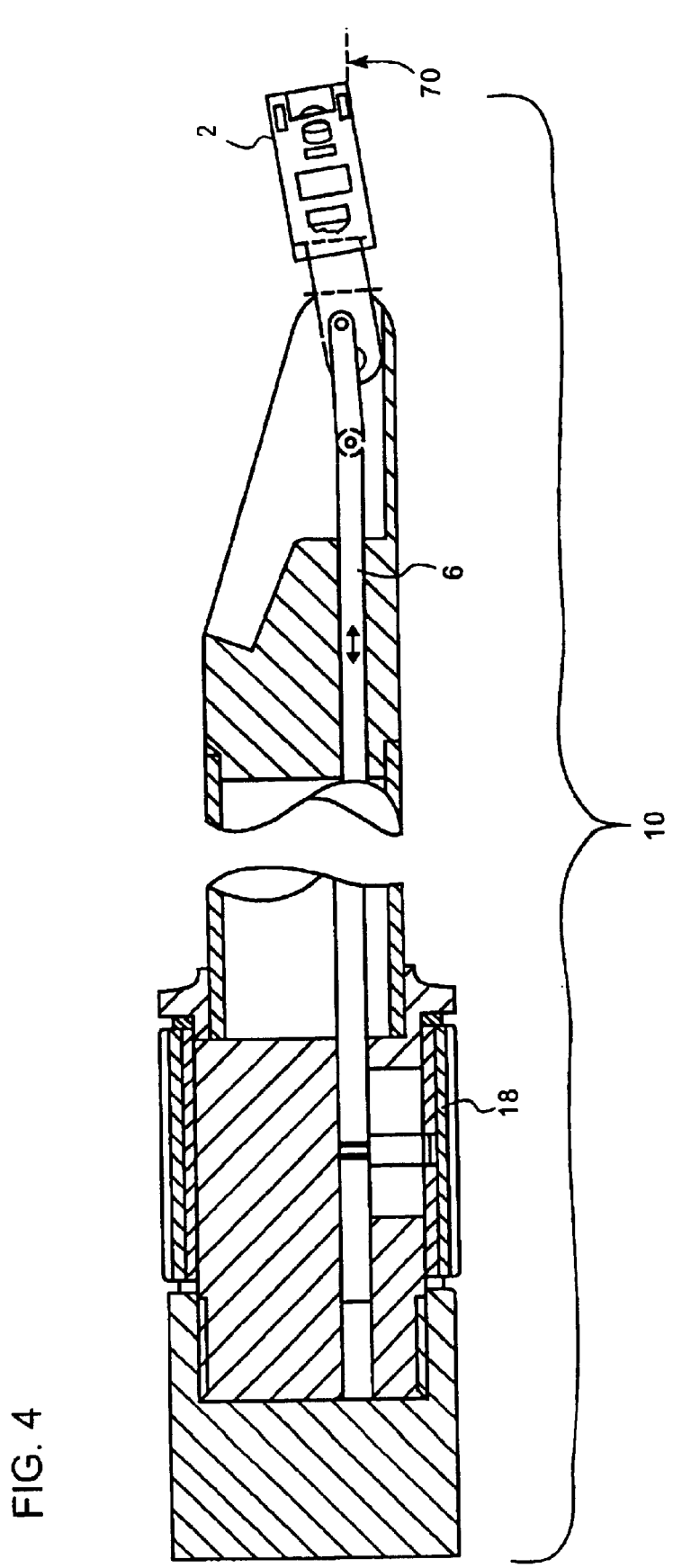
FIG. 4 is a cross-sectional side view of the endoscope of FIG. 2 with the imaging probe in an extended position.

Referring to FIG. 4, prior to insertion with patient 99, for example through an introducing cannula (not shown), the surgeon rotates outer adjustment ring 18 in a counterclockwise direction to cause imaging probe 4 to rotate to its fullest extent so that imaging probe 2 is about 5–10° above longitudinal axis 70.

Referring back to FIG. 2, once endoscope 10 is positioned within the body cavity near target object 23, the surgeon can rotate outer adjustment ring 18 in a clockwise direction, which moves push rod 6 away from the distal end 7 and correspondingly rotates imaging probe 2 in counterclockwise direction 75 away from target object 23. Imaging probe 2 can rotate about fixed point 8 as much as approximately 160° degrees. As explained below, main shaft 41 can also be rotated 360° about axis 70. Thus, the effective field of view of endoscope 10 will constitute a full 360° solid angle less some shadow area caused by shaft 41.

Figure 5:
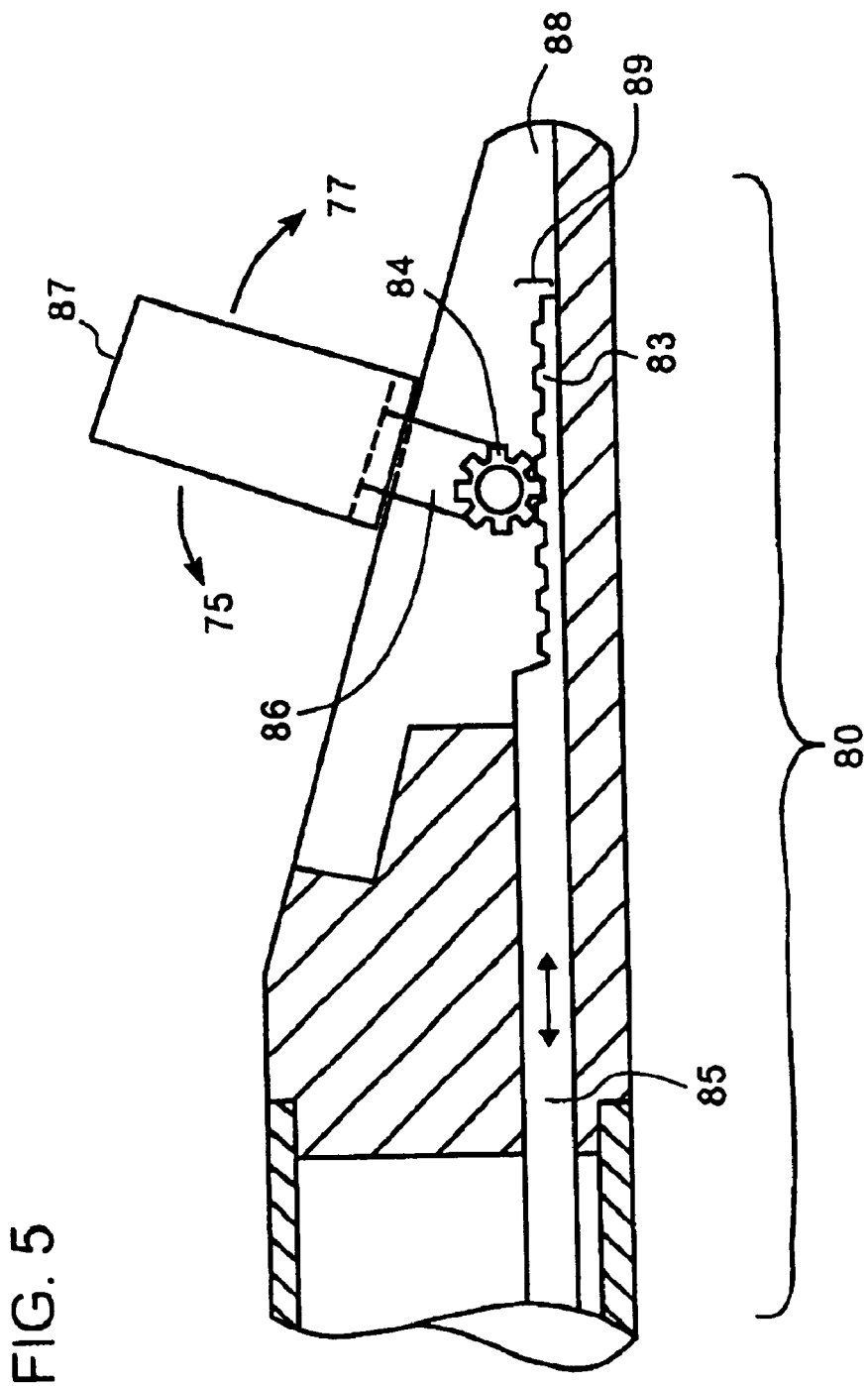
FIG. 5 shows the distal end of an alternative embodiment of an endoscope.

Other embodiments are within the scope of the claims. For example, other actuating assemblies can be used to rotate the imaging probe relative to the fixed point. For example, referring to FIG. 5, a rack and pinion assembly 80 is used to rotate imaging probe 87. In this embodiment, a rack 83 having a number of teeth 89 is provided at a distal end 88 of push rod 85. Teeth 89 mesh with a pinion 84 fixed to an arm 86 pivotably connected to the distal end of elongated shaft and supporting imaging probe 87. When rod 85 is pushed or pulled, rack 83 moves axially causing pinion 84 to rotate and, in turn, move imaging probe 87. In particular, moving rack 83 towards the distal end of endoscope moves imaging probe 87 in a counterclockwise direction 77, while moving rack 83 away from the distal end moves the imaging probe in clockwise direction 75 relative to axis 70.

Figure 6:
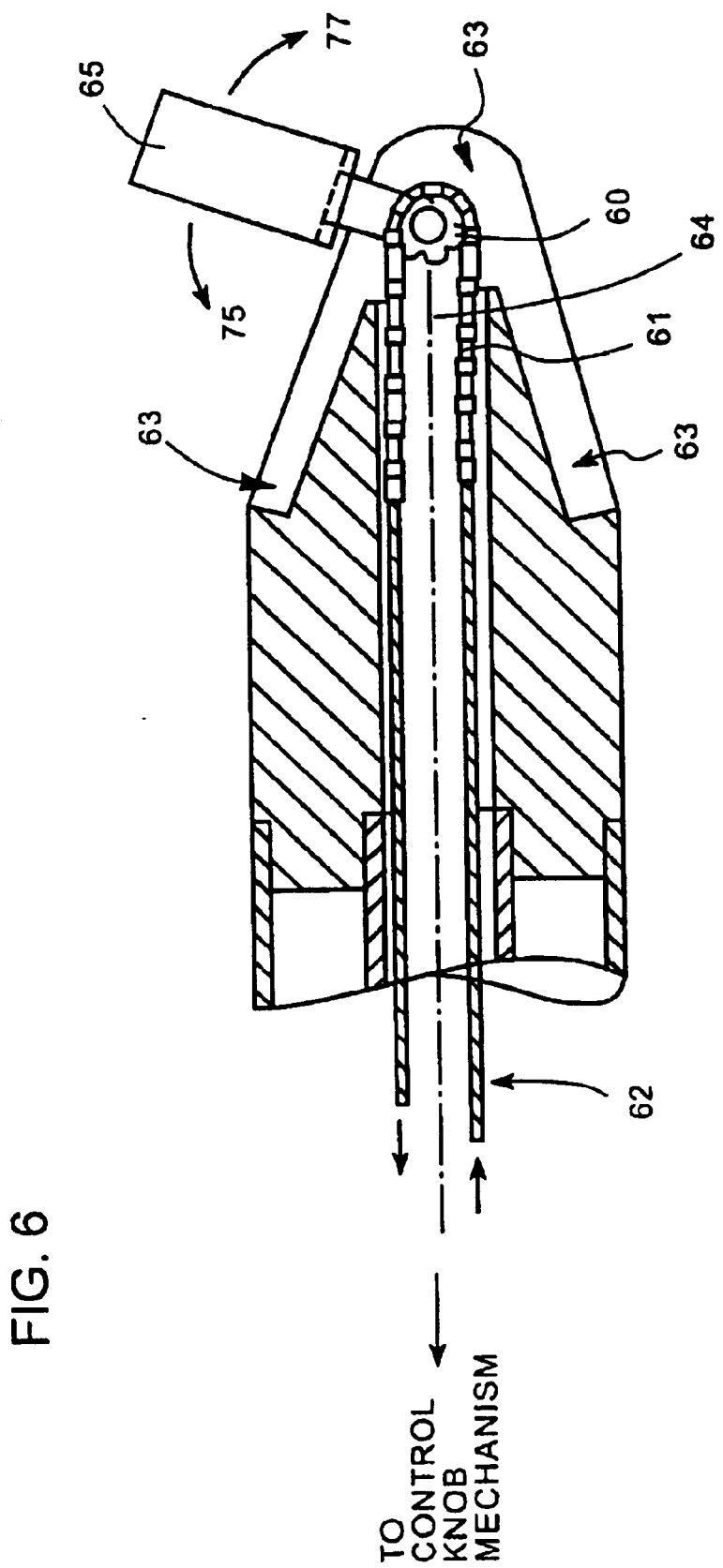
FIG. 6 shows the distal end of another alternative embodiment of an endoscope.

Referring to FIG. 6, another alternative actuating assembly includes a chain and sprocket assembly instead of a push rod. In this embodiment, imaging probe 65 is fixed to a sprocket 60. Sprocket 60 is driven by a miniature chain 61. For example, chain 61 can be a section of an angulation control cable 62 that extends to proximal end 5 of endoscope 10 where a similar chain and sprocket device connected to a control knob (not shown) is used. By having a channel 63 that extends around a distal end 64, the imaging probe 65 can rotate more than 270° rotation about sprocket 60 or almost twice the rotation of a push rod assembly.

Figure 7:
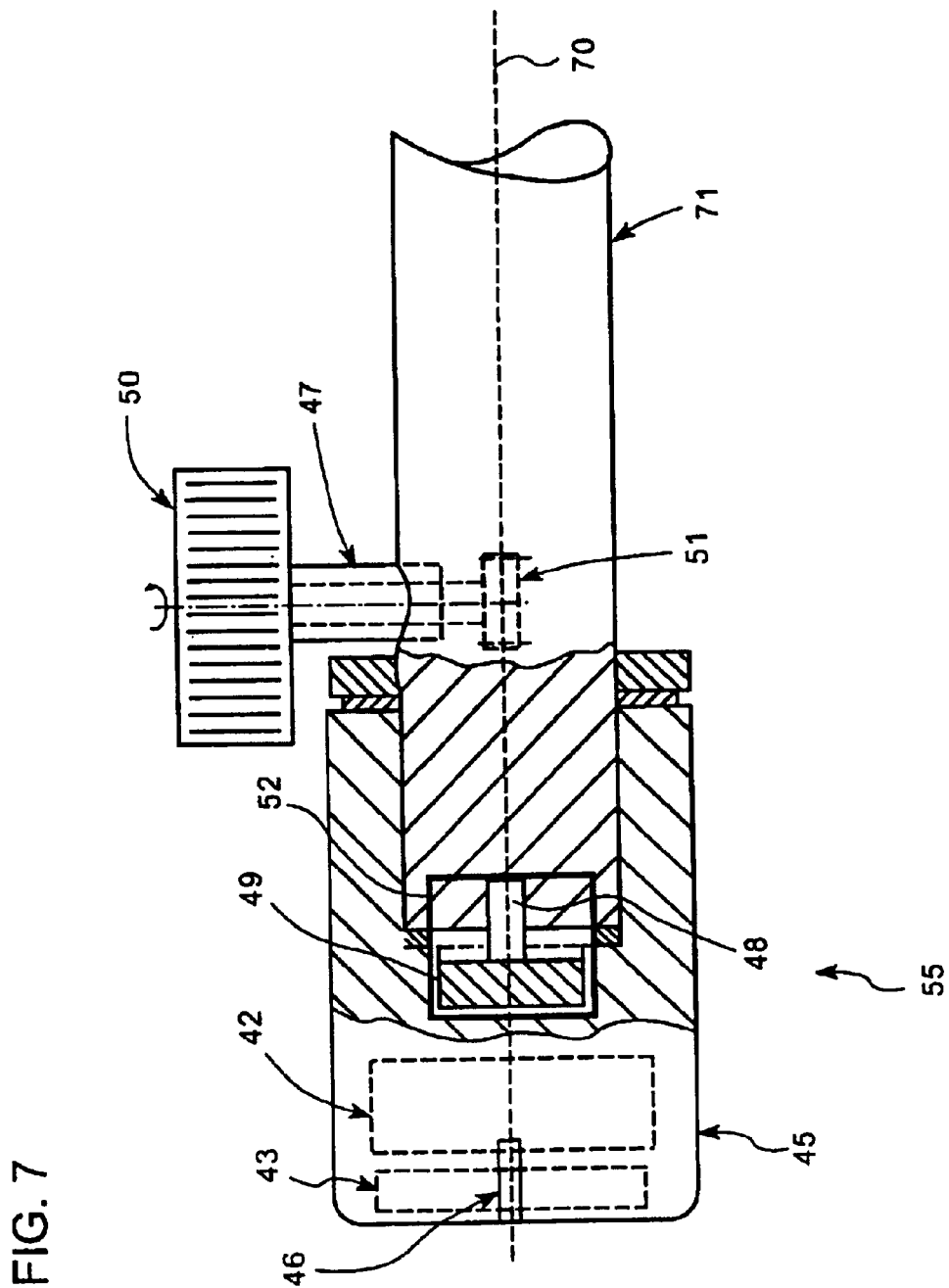
FIG. 7 is a proximal end of the endoscope of FIG. 2.

With reference back to FIG. 3 and referring to FIG. 7, in another embodiment of an endoscope 55, a battery pack 42 and a transceiver 43 are positioned at a handle 45 where transceiver 43 receives power from battery pack 42. In this embodiment, transceiver 43 receives images from transmitter 26 and relays those images to external receiver 33. Because the signal is transmitted wirelessly from imaging probe 2 to handle 45 at proximal end 5, wiring between handle 45 and the imaging probe (not shown) at the distal end (not shown) of the endoscope is no longer required. Also, because the distance between transmitter 26 and transceiver 43 is relatively short (approximately 300 mm), the amount of battery power required to supply transmitter 26 is relatively low. Requiring transmitter 26 to transmit signals directly to external receiver 33 (3 to 4 meters away) would require substantially much greater power. Furthermore, minimizing the power requirements of the battery, reduces the size of the battery itself, as well as the overall size of imaging probe 2. In certain embodiments, transmitter 26 and battery 28 may be positioned inside shaft 41 to further reduce the size of the imaging probe.

Handle 45 is connected to a shaft 71 such that shaft 71 rotates with respect to the handle. Because shaft 71 can be rotated about a longitudinal axis 90 of the endoscope, coverage of the effective field is close to 360°. However, sensor 24 will also rotate with shaft 71. When shaft 71 is rotated 180° (half rotation), the orientation of the image will be reversed. Reversal of the image in certain surgical applications may confuse the surgeon in knowing which end is up when viewing the image of on a monitor. To address this problem, handle 45 has an indicator 46 (e.g., a rib, a flute, buttons) that indicates its "right side up" position. Shaft 71 has a pin 47 which is used for convenient single-hand actuated rotation relative to handle 45. Pin 47 is connected to an angulation control knob 50 and a driving gear 51. Gear 51 may be in the form of a pinion driving the rack or it may be a sprocket driving a chain mechanism.

In operation, knob 50 has two functions. In the first function, knob 50 is turned either clockwise or counter clockwise. Each turn of knob 50 rotates the imaging sensor (not shown). In a second function, applying a force perpendicular to knob 50 will rotate shaft 71 when the surgeon holds handle 45 in fixed position. Thus, handle 45 position is maintained in a "right side up" position while shaft 71 is rotated with respect to handle 45. Proximal end of shaft 71 is connected to a rotor 48 of an angle position sensor 52, such as a potentiometer or magnetic angle sensor. Stator 49 of angle sensor 52 is fixed to handle 45. During the operation, the angle between the "up" position and the current position of shaft 41 is constantly monitored. This information is transmitted to a camera control unit via cable or wirelessly. The camera control unit processes the rotation angle information and enables respective rotation of the image on monitor 35 to preserve the "right side up" image orientation. To prevent potential jitter, the image rotation may take place at discrete positions, such as 10° intervals.

As described above, swiveling imaging probe advantageously allows the surgeon to view target areas over relatively large ranges of observation. Referring to FIGS. 8 and 9, another advantage of swiveling the imaging probe about a fixed point 88 is that when the imaging probe is in its fully retracted position, that is, "looking back" toward a shaft 81, objective lens 92 can be conveniently and efficiently washed and dried without removing the imaging probe from the cavity. An air/water conduit 83 inside shaft 81 and above a push arm 96 is connected at a section 95 of shaft 81 to an air valve 85 and a water valve 84 where air valve 85 is connected to an air supply and water valve 84 is connected to a water supply. The air/water conduit extends away from air valve 85 and water valve 84 to an opening 86 at a distal end 87. As imaging probe 82 reaches a retracted profile position and with water valve 84 open and air valve 85 closed, objective lens 92 may be effectively sprayed with a water stream directly towards lens 92. This design is unlike other systems where the stream of water is directed tangentially to objective lens 92. After spraying water on objective lens 92, water valve 84 is closed and air valve 85 is opened so that the air may be applied to dry objective lens 92. Other fluids may be used to wash and dry objective lens 92.

Still other embodiments are within the scope of the following claims.

What is claimed is:

1. An endoscope comprising:
    an elongated member having a longitudinal axis and a passage extending from a proximal end to a distal end of the elongated member;
    an imaging probe positioned at the distal end of the elongated member and including:
        an objective lens;
        an imager positioned to receive an image from the objective lens; and
        a light source for illuminating a target;
    a pivot mechanism; and
    an actuating assembly extending through the passage of the elongated member and coupled to the pivot mechanism, the actuator assembly including an actuator, wherein upon actuation of the actuator, the pivot mechanism rotates the imaging probe relative to a point at the distal end of the elongated member;
    wherein the imaging probe is detachably secured to the pivot mechanism and configured to rotate about the longitudinal axis of the elongated member relative to a stationary handle at the proximal end of the elongated member when applying a force perpendicular to the actuator;
    wherein the elongated member includes a conduit having a first port at the proximal end of the elongated member and attached to a fluid source and a second port at the distal end of the elongated member and positioned to discharge fluid on the objective lens.

2. The endoscope of claim 1 wherein the pivoting mechanism includes an arm that swivels about the point.

3. The endoscope of claim 1 wherein the actuating assembly includes a chain located at the distal end of the elongated member and a sprocket is coupled to the chain.

4. The endoscope of claim 1 wherein the actuating assembly includes a push rod assembly.

5. The endoscope of claim 4 wherein the push rod assembly includes a pinion and a rack, the rack coupled to a pinion and extending substantially parallel with the longitudinal axis of the elongated member.

6. The endoscope of claim 1 wherein the actuating mechanism includes a rotatable ring positioned at the proximal end of the elongated member.

7. The endoscope of claim 1 wherein the conduit further comprising a third port at the proximal end of the elongated member and connected to an air source.

8. An endoscope comprising:
an elongated member having a longitudinal axis and a passage extending from a proximal end to a distal end of the elongated member;
an imaging probe positioned at the distal end of the elongated member and including:
an objective lens;
an imager positioned to receive an image from the objective lens;
a light source for illuminating a target;
a transmitter; and
a first power source electrically connected to the transmitter;
a pivot mechanism mechanically coupled to the imaging probe;
a transceiver located at the proximal end of the elongated member that receives signals from the transmitter and transmits the signals to a receiver that is external to the endoscope;
an actuating assembly extending through the passage of the elongated member and coupled to the pivoting mechanism, wherein upon actuation of the actuating mechanism, the pivot mechanism rotates the imaging probe relative to a point at the distal end of the elongated member.

9. The endoscope of claim 8 further comprising a second power source positioned at the proximal end of the elongated member and electrically connected to the transceiver.

10. The endoscope of claim 8 further comprising an angle position sensor configured to provide information to a camera control unit to maintain a right side up image while the imaging probe rotates about the longitudinal axis.

11. An endoscope comprising:
an elongated member having a longitudinal axis and a passage extending from a proximal end to a distal end of the elongated member;
an imaging probe positioned at the distal end of the elongated member, the imaging probe including:
an objective lens;
an imager positioned to receive an image from the objective lens;
a transmitter electrically connected to the imager;
a light source for illuminating a target; and
a first power source for supplying power to the transmitter and the light source;
a transceiver located at the proximal end of the elongated member, the transceiver receiving signals from the transmitter and transmitting the signals to a receiver external to the endoscope.

12. The endoscope of claim 11 further comprising a second power source positioned at the proximal end of the elongated member and electrically connected to the transceiver.

13. The endoscope of claim 11 further comprising:
a pivot mechanism mechanically coupled to the imaging probe; and
an actuating assembly extending through the passage of the elongated member and coupled to the pivoting mechanism, wherein upon actuation of the actuating mechanism, the pivot mechanism rotates the imaging probe relative to a point at the distal end of the elongated member.

14. The endoscope of claim 13 wherein the actuating mechanism includes a rotatable ring positioned at the proximal end of the elongated member.

15. The endoscope of claim 13 wherein the pivoting mechanism includes an arm that swivels about the point.

16. The endoscope of claim 13 wherein the actuating assembly includes a chain located at the distal end of the elongated member and a sprocket is coupled to the chain.

17. The endoscope of claim 13 wherein the actuating assembly includes a push rod assembly.

18. The endoscope of claim 17 wherein the push rod assembly includes a pinion and a rack, the rack coupled to a pinion and extending substantially parallel with the longitudinal axis of the elongated member.

19. The endoscope of claim 11 wherein the elongated member includes a conduit having a first port at the proximal end of the elongated member and attached to a fluid source and a second port at the distal end of the elongated member and positioned to discharge fluid on the objective lens.

20. The endoscope of claim 19 wherein the conduit further comprising a third port at the proximal end of the elongated member and connected to an air source.

21. The endoscope of claim 11 wherein the imaging probe is configured to rotate about the longitudinal axis of the elongated member relative to a stationary handle located at the proximal end of the elongated member.

22. The endoscope of claim 21 further comprising an angle position sensor configured to provide information to a camera control unit to maintain a right side up image while the imaging probe rotates about the longitudinal axis.

* * * * *